US00PP11812P2

(12) United States Plant Patent
van Rijn

(10) Patent No.: US PP11,812 P2
(45) Date of Patent: Mar. 13, 2001

(54) ANTHURIUM PLANT NAMED 'SACHA'

(75) Inventor: Leonardus van Rijn, Schipluiden (NL)

(73) Assignee: RijnPlant, Schipluiden (NL)

( * ) Notice: Subject to any disclaimer, the term of this patent is extended or adjusted under 35 U.S.C. 154(b) by 0 days.

(21) Appl. No.: 09/291,097

(22) Filed: Apr. 14, 1999

(51) Int. Cl.[7] ..... A01H 5/00
(52) U.S. Cl. ..... Plt./365
(58) Field of Search ..... Plt./365, 369

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Anthurium plant named 'Sacha', characterized by its upright plant habit; freely clumping growth habit; durable and large dark green leaves that are ovate in shape; numerous spathes that are positioned upright and beyond the foliage on strong and erect scapes; large, durable, glossy red spathes; year-round continuous flowering; good flowering performance under low light conditions; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name Sacha.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor in April, 1994 of the Inventor's proprietary *Anthurium andreanum* selection code number 00-25 as the female, or seed, parent with the Inventor's proprietary *Anthurium andreanum* selection code number 93-2 as the male, or pollen, parent. The cultivar Sacha was discovered and selected by the Inventor as a plant within the progeny of the stated cross in a controlled environment in Schipluiden, The Netherlands in July, 1996.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Sacha. These characteristics in combination distinguish 'Sacha' as a new and distinct cultivar:

1. Upright plant habit.

2. Freely clumping growth habit.

3. Durable and large dark green leaves that are ovate in shape.

4. Numerous spathes that are positioned upright and beyond the foliage on strong and erect scapes.

5. Large, durable, glossy red spathes.

6. Year-round continuous flowering.

7. Good flowering performance under low light conditions.

8. Good post-production longevity.

The new Anthurium can be compared to the female parent, the Inventor's proprietary selection code number 00-25. In side-by-side comparisons conducted by the Inventor in Schipluiden, The Netherlands, plants of the new Anthurium differ from plants of selection code number 00-25 in the following characteristics:

1. Plants of the new Anthurium are more compact than plants of the selection code number 00-25.

2. Plants of the new Anthurium have smaller spathes than plants of the selection code number 00-25.

3. Plants of the new Anthurium have red-colored spathes whereas plants of the selection code number 00-25 have pink-colored spathes.

The new Anthurium can be compared to the male parent, the Inventor's proprietary selection code number 93-2. In side-by-side comparisons conducted by the Inventor in Schipluiden, The Netherlands, plants of the new Anthurium differ from plants of selection code number 93-2 in the following characteristics:

1. Plants of the new Anthurium have smaller and softer leaves as plants of the selection code number 93-2.

2. Plants of the new Anthurium have red-colored spathes whereas plants of the selection code number 93-2 have pink-colored spathes.

The new Anthurium can be compared to the Anthurium cultivar Jolanda, not patented. In side-by-side comparisons conducted by the Inventor in Schipluiden, The Netherlands, plants of the new Anthurium differ from plants of the cultivar Jolanda in the following characteristics:

1. Plants of the new Anthurium have more durable and rougher leaves than plants of the cultivar Jolanda.

2. Plants of the new Anthurium and of the cultivar Jolanda differ in spathe coloration.

BRIEF DESCRIPTION OF THE PHOTOGRAPH

The accompanying colored photograph illustrates the overall appearance of the new Anthurium, showing the colors as true as it is reasonably possible to obtain in colored reproductions of this type.

The photograph comprises a side perspective view of a typical potted plant of the cultivar Sacha. Leaf, spathe and spadix colors in the photograph may appear different from the actual colors due to light reflecance.

DETAILED BOTANICAL DESCRIPTION

In the following description, color references are made to The Royal Horticultural Society Colour Chart except where general terms of ordinary dictionary significance are used. The following observations and measurements describe 2.5-years old plants grown in 17-cm containers in Schipluiden, The Netherlands, in a glass greenhouse with an average day temperature of 25° C. and an average night temperature of 19° C.

Botanical classification: *Anthurium andreanum* cultivar Sacha.

Parentage:

*Female parent.*—Inventor's proprietary *Anthurium andreanum* selection code number 00-25.

*Male parent.*—Inventor's proprietary *Anthurium andreanum* selection code number 93-2.

Propagation:

*Method.*—By tissue culture.

*Time to develop roots.*—About 70 or 84 days at 24° C., respectively are required to root a tissue-cultured plantlet.

*Rooting habit.*—Numerous and very strong fleshy roots.

Plant description:

*Plant shape.*—Upright, inverted triangle, symmetrical.

*Growth habit.*—Freely clumping, bushy and dense; about ten shoots per plant. Appropriate for 17 to 40-cm containers.

*Plant height.*—About 50 to 60 cm from soil level to apex of spathes.

*Plant width*—About 70 to 80 cm.

*Plant vigor.*—High.

*Growth rate.*—Rapid.

*Crop time.*—About 8 and 16 months are usually required from planting of young plants to finished plants in 17 and 40-cm containers, respectively.

*Foliage description.*—Quantity: Usually about two or three per shoot. Length: About 22 to 34 cm. Width: About 13 to 19 cm. Shape: Ovate; slightly lanceolate. Apex: Apiculate to aristate. Base: Strongly auriculate; lobes not overlapping. Margin: Entire. Texture: Smooth, glabrous, leathery. Color: Young leaves, upper surface: 144A to 146A. Young leaves, lower surface: 146D with gray and red tones. Mature leaves, upper surface: Darker than 137A. Mature leaves, lower surface: 144A to 146C. Petiole: Length: About 24 to 38 cm. Color: Close to 146A, moderate purple anthocyanin. Geniculum length: About 2.5 to 3.5 cm. Geniculum diameter: About 4 to 6 mm. Geniculum color: 144A: slight purple anthocyanin.

Inflorescence description:

*Inflorescence arrangement.*—Spathes with spadices held beyond the foliage. Flowering structures arise from leaf axils. Freely flowering; continuous flowering year-round, numerous spathes/spadices per plant.

*Inflorescence longevity.*—Spathes/spadices last about six weeks under winter conditions and about three months under summer conditions; persistent.

*Flowers.*—Quantity per spadix: Numerous, about 150 to 200. Shape: Rounded. Diameter: About 1 mm, maximum.

*Spathe.*—Length: About 8 to 11 cm. Width: About 7 to 9 cm. Shape: Oblong, narrowly cordate. Apex: Apiculate to cuspidate. Base: Strongly auriculate, lobes not overlapping. Margin: Entire. Texture: Leathery, glabrous, moderate blistering, glossy. Color: When opening: 46B to 47C. Front surface: 45A to 46B. Back surface: 47C to 46C. After senescence: 47B, dull.

*Spadix.*—Length: About 5 to 6 cm. Diameter: Midsection, about 8 to 10 mm; apex, about 5 to 6 mm. Shape: Columnar. Cross section: Rounded. Longitudinal axis: Very weakly recurved; about 45° C. to spathe. Color: Base and mid-section: 158C. Apex: 24A. After senescence: Entire spadix initially 50B, then 137A.

*Scape.*—Length: About 35 to 45 cm. Aspect: Strong and erect, slight bending. Color: 146A, overlaid with anthocyanin towards apex, close to 185B.

*Reproductive organs.*—Androecium: Pollen color: Creamy white, 158D. Gynoecium: Stigma shape: Ovoid. Ovary: Protogyneous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Sacha', as illustrated and described.

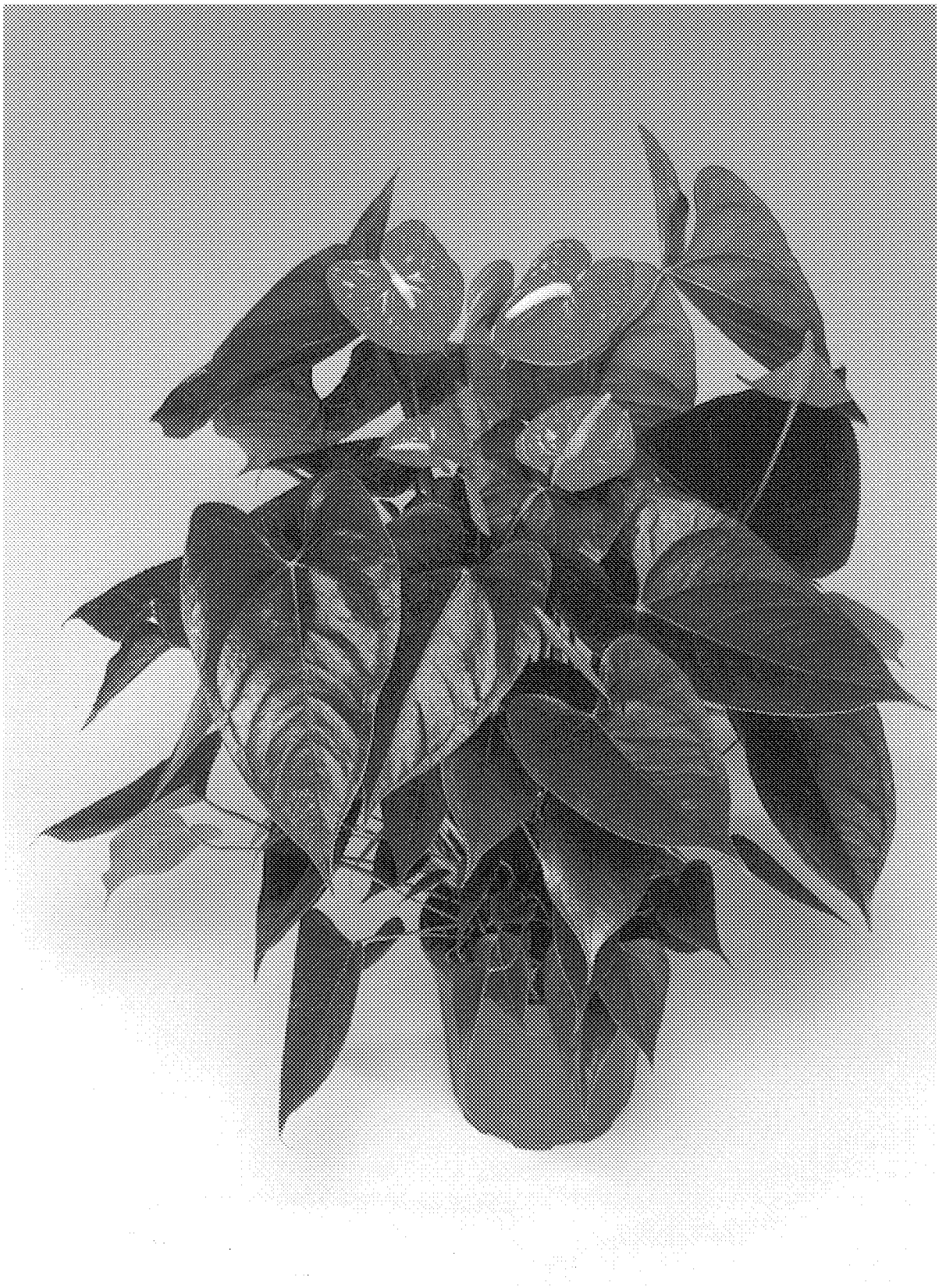

* * * * *